United States Patent [19]

Allen

[11] 4,266,084

[45] May 5, 1981

[54] NON-CATALYTIC PYROLYSIS OF RESIDUES FROM AROMATIC CARBOXYLIC ACID MANUFACTURE

[75] Inventor: John K. Allen, St. Charles, Ill.

[73] Assignee: Standard Oil Company (Indiana), Chicago, Ill.

[21] Appl. No.: 86,403

[22] Filed: Oct. 19, 1979

[51] Int. Cl.³ .............................................. C07C 1/20
[52] U.S. Cl. .................................... 585/469; 585/606; 585/733; 260/346.4
[58] Field of Search ...................... 585/469, 606, 733; 260/346.4

[56] References Cited

U.S. PATENT DOCUMENTS

| | | | |
|---|---|---|---|
| 3,862,145 | 1/1975 | Brennan et al. | 260/346.4 |
| 4,097,541 | 6/1978 | Sakai et al. | 585/469 |

Primary Examiner—Veronica O'Keefe
Attorney, Agent, or Firm—Fred R. Ahlers; William T. McClain; William H. Magidson

[57] ABSTRACT

Commercially attractive amounts of benzene and toluene can be obtained from a solid mixture of aldehydo-, carboxy-, keto- and carboxy-, carboxy- and aldehydo-substituted benzene and toluene including such mixtures also containing cobalt and manganese salts of organic acids and inorganic and organic bromides obtained from the manufacture of benzene di- and tricarboxylic acids by non-catalytic pyrolysis of such mixture or gases and vapors therefrom at a temperature of at least 700° C. Such non-catalytic pyrolysis is more technically attractive than catalytic pyrolysis conducted at a temperature of from 300° C. to 500° C. which has a short activity life.

6 Claims, No Drawings

NON-CATALYTIC PYROLYSIS OF RESIDUES FROM AROMATIC CARBOXYLIC ACID MANUFACTURE

FIELD OF INVENTION

This invention relates to the recovery of aromatic compound values from residues obtained in the manufacture of an aromatic di- or tricarboxylic acid. More specifically the present invention pertains to a non-catalytic pyrolysis conducted at an elevated temperature of at least 700° C. with a mixture of oxygen-containing derivatives of benzene and toluene containing a cyclic ester group (e.g., as in phthalide) and one or more aldehydo-, methylol-, carboxy-nuclear substituents.

STATE OF THE ART

The thermal decomposition of benzoic acid to benzene and carbon dioxide begins non-catalytically at 370° C. in a glass bulb and is substantially complete at 400° C. (Chemical Abstracts, vol. 41, 646) according to the original article of Wolfgang Mosher in Helv. Chem. Acta. 14, 971–97 (1931) and such dissociation is accelerated by copper and cadmium catalysts. Said dissociation occurs at temperatures as low as 245° to 250° C. in the presence of Zn-Cu-Cr oxide-type catalysts according to Corliss R. Kinney and David P. Langlois in J. Am. Chem. Soc. vol. 53, 2189–2192 (1931). Decarbonylation of benzaldehyde to high yields of benzene is aided by plasma of glow discharge according to Published Patent Application ("Offenlegungsschrift") 2,038,272 of the Federal German Republic published 16 March 1972. According to British Pat. No. 735,300 published 17 August 1955, toluic acids heated to 400° C. in the presence of chromites of Zn, Cd, Zn-Cd, Zn-Fe or ZnO with either CuO or CdO are converted to toluene.

The preparation of benzoic acid by the thermal decarboxylation of phthalic acids in the presence of steam is known to be generally conducted in the presence of a catalyst such as nickel phthalate at 175° to 350° C. according to U.S. Pat. No. 1,962,175; 1 to 2% ammonia in the steam according to British Pat. No. 469,541 published 27 July 1932; $V_2O_5$ or ZnO on $Al_2O_3$ or $Al_2O_3$ alone according to Chemical Abstracts vol. 37, Col. 5383; carbon catalyst impregnated with hydroxides of both alkali and alkaline earth metals to effect the decarboxylation at temperatures at and below 400° C. according to U.S. Pat. No. 2,470,688; cobalt carbonyl, $Co_2(CO)_8$ used in an atmosphere of carbon monoxide and hydrogen converts phthalic acids and substituted phthalic acids to benzoic acid and substituted benzoic acid or cobalt carbonyl modified by trialkylphosphine ligands converts benzene polycarboxylic acids having COOH groups on adjacent ring carbon atoms to iso- and terephthalic acids according to Chemical Abstracts vol 81 entry 52064r. Also heating trimellitic acid to temperatures of 300° to 375° C. converts the tricarboxylic acid to o-phthalic acid according to U.S. Pat. No. 3,862,145.

From the state of the art at the time of making the present invention it appears that the main interest in decarboxylation of benzene carboxylic acids was to prepare a higher quality benzene carboxylic acid of lesser COOH group content from a benzene carboxylic acid of higher COOH group content and lower quality such as a coal acid or to obtain a benzene carboxylic acid of exceptionally high quality; e.g., pharmaceutical quality benzoic acid, from phthalic anhydride by converting it to o-phthalic acid and decarboxylating it. But there was no apparent interest in the decarboxylation of benzene carboxylic acids to aromatic hydrocarbons.

In an altogether different environment a new problem has arisen. In the commercial manufacture of benzene di- or tricarboxylic acids (e.g., isophthalic acid, terephthalic acid or trimellitic acid) there is obtained, after maximizing recovery of such acid and recovering for reuse the reaction solvent, a residue which is a mixture of oxygen-containing derivatives of benzene and toluene which are mono-, di- and tricarboxylic acids, aldehydo-carboxylic acids, and methylol-substituted benzene or toluene or their carboxylic (benzoic or toluic) acids and which also contains components of catalysis. Usually such components of catalysis are Co-Mn-Br or Co-Mn-Ce-Br from liquid phase oxidation of a xylene or pseudocumene (1,2,4-trimethylbenzene) with air in the presence of acetic acid reaction solvent. A similar residue is also obtained from the next oxidation of liquid o-xylene with air in the presence of Co-Mn-Br catalyst system after dehydrating the o-phthalic acid formed to its anhydride under conditions which vaporize the anhydride, water and materials boiling between the anhydride and water. While such residues amount to from 2 to 25 weight percent of the benzene di- or tricarboxylic acid produced, such residue production annually is substantially in view of the millions of kilograms of the benzene di- or tricarboxylic acids produced annually.

Such residues contain water soluble benzene carboxylic acids and water soluble forms of the components of catalysis. Landfill disposal of such residues is undesirable because rain and ground water leach out those carboxylic acids and soluble forms of the components of catalysis and can contaminate surface run off water and eventually streams as well as below surface aquafiers. Disposal of such residues can be made by incineration and use made of the resultant heat produced but the catalyst components are converted to forms in the resultant ash which are difficult and/or expensive to convert to reusable forms for the oxidation of the methyl-substituted benzenes. Although in such residues the substituted benzene and toluene compounds whose substituents are the carboxy-, aldehydo- and methylol substituents are individually desirable and useful commercial products it is not economically feasible to separate and recover the individual compounds from the residues.

Based on the knowledge that most of the oxygen-containing aromatic compounds in the residue can be decarboxylated and/or decarbonylated by thermal means, it would be desirable to devise a decarboxylation and/or decarbonylation process which would convert the oxygen-containing aromatic compounds to aromatic hydrocarbons which are volatile under such process conditions so that the hydrocarbon vapors can be readily removed and condensed for their recovery. It is also known that under the severe thermal conditions required for substantially complete decarboxylation and/or decarbonylation to convert the oxygen-containing substituted aromatics to benzene and toluene there can also occur ring coupling (e.g. to form biphenyl) and ring fusion as well as charring of some of the organic compounds.

To use a decarboxylation and/or decarbonylation catalyst for the thermal conversion of the foregoing residues to easily recoverable and useful aromatic hydrocarbons would be desirable providing the use of catalyst does enhance the production of the aromatic hydrocarbons but does not make useless the resulting char or further contaminate the catalyst components present so as to make the recovery of cobalt, the most expensive component, technically and commercially unattractive.

We have in our laboratories investigated the use of various compositions previously suggested as decarboxylation catalyst and found the resulting thermal conversions to be unattractive.

There follows in TABLES I and II the results of vapor phase decarboxylation of a single benzene carboxylic acid by vaporizing the acid at one temperature and then contacting the vapors with a catalyst sometimes at a second temperature as indicated. Further, in such decarboxylation the catalyst is first placed in a quartz tube, the tube is heated in two zones with electric furnaces, and the benzene carboxylic acid sample is inserted into the vaporizing section of the tube in a ceramic boat, said boat is moved into and out of the vaporizing portion of the tube by a nichrome wire attached to the boat. Vaporization of the sample is accomplished in 5 to 15 minutes at the 500° C. temperature. A small nitrogen gas flow (about 3 ml/sec) through the tube is used to sweep the vapors through the hot catalyst and out of the tube. Products of the decarboxylations are collected by transport of the gaseous mixture after contact with the catalyst through two cooled traps, then through a drier to remove water vapor and then to a gas collector. At least one of the traps is cooled with a mixture of crushed solid $CO_2$ and isopropyl alcohol. Measured samples of the collected gas are analyzed by mass spectrometry. For the present purpose of illustrating the effectiveness of prior suggested catalysts, only the total amount of liquid aromatic hydrocarbons collected in the cooled traps and the amount of $CO_2$ generated expressed as weight percentages of the benzene carboxylic acid used are reported.

Except for two decarboxylations in TABLE I illustrating the use of zinc oxide and zinc oxide supported on alumina as the catalyst, the benzene carboxylic acid samples subjected to decarboxylation were about one gram in size. Those two exceptions used five gram samples supplied by five one gram samples successively introduced into the vaporizing portion of the tubes.

TABLE I
DECARBOXYLATION OF TEREPHTHALIC ACID

| | Catalyst | Temperature, °C. Vap. | Temperature, °C. Catalyst | Product, Wt. % Liquid | Product, Wt. % $CO_2$ |
|---|---|---|---|---|---|
| 4789-151 | Ba Promoted Cu Chromite | 352 | 352 | 3.97 | 64.5 |
| -150 | " | 399 | 399 | 7.99 | 127.7 |
| -156 | $Cu_2O_3$—ZnO | 400 | 400 | 11.9 | 102.3 |
| -147 | Ni Oxide on Alumina | 446 | 446 | 18.0 | 45.4 |
| -155 | ZnO | 511 | 511 | 24.0 | 39.9 |
| -165 | ZnO-Chromia | 499 | 499 | 3.8 | 49.2 |
| -184 | Zn Chromite | 499 | 499 | 21.8 | 67.9 |
| -185 | Chromia-Alumina-Magnesia | 500 | 500 | 17.7 | 46.3 |
| -188 | K Promoted Chromia-Alumina | 499 | 499 | 20.8 | 66.1 |
| -195 | ZnO-Alumina | 498 | 498 | 33.9 | 29.0 |
| -200 | ZnO—$MoO_2$ on Molecular Sieve | 499 | 499 | 31.7 | 26.8 |
| -204 | ZnO—$Co_2O_3$—$W_2O_3$ on Molecular Sieve | 500 | 500 | 33.0 | 48.8 |

TABLE I-continued
DECARBOXYLATION OF TEREPHTHALIC ACID

| | Catalyst | Temperature, °C. Vap. | Temperature, °C. Catalyst | Product, Wt. % Liquid | Product, Wt. % $CO_2$ |
|---|---|---|---|---|---|
| 5065-001 | ZnO—$Co_2O_3$—$MoO_2$ on Molecular Sieve | 500 | 500 | 22.0 | 39.3 |
| -005 | Chromia on Molecular Sieve | 499 | 499 | 17.0 | 41.3 |
| -006 | ZnO* | 501 | 501 | 24.3 | 23.0 |
| -007 | ZnO on Alumina* | 500 | 500 | 32.9 | 36.3 |
| -010 | ZnO-Alumina | 500 | 500 | 33.0 | 47.9 |
| -022 | " | 499 | 498 | 36.9 | 47.3 |
| -023 | " | 501 | 399 | 0 | 19.9 |
| -025 | " | 500 | 451 | 26.9 | 40.6 |
| -030 | CaO | 500 | 502 | 25.9 | 0.04 |
| -031 | $CaCO_3$ | 499 | 501 | 5.0 | 29.9 |
| -036 | CdO | 499 | 502 | 22.0 | 38.8 |

*Five grams terephthalic acid

The theoretical amounts of benzene and carbon dioxide from the complete decarboxylation of terephthalic acid are, respectively, 47 weight percent and 53 weight percent. The above amounts of $CO_2$ reported in excess of said 53 wt.% may be from partial combustion of the benzene produced.

TABLE II
DECARBOXYLATION AND/OR DECARBONYLATION OF BENZOIC ACID AND SUBSTITUTED BENZOIC ACIDS IN THE PRESENCE OF ZINC OXIDE ON ALUMINA

| | Acid | Temperature, °C. Vap. | Temperature, °C. Catalyst | Product, Wt. % Liquid | Product, Wt. % $CO_2$ |
|---|---|---|---|---|---|
| 4789-149 | Benzoic Acid* | 399 | 399 | 19.9 | 12.26 |
| 5065-037 | Benzoic Acid | 501 | 501 | 53 | 29.7 |
| -011 | Isophthalic Acid | 500 | 500 | 33 | 45.4 |
| -012 | o-Phthalic Acid | 497 | 499 | 24 | 37.2 |
| -014 | p-Toluic Acid | 501 | 501 | 21 | 21 |
| -015 | Trimellitic Acid | 502 | 502 | 13 | 32.8 |
| -016 | 4-Carboxy-benzaldehyde | 500 | 500 | 18.4 | 31.1 |
| -017 | Phthalic Anhydride | 502 | 502 | 20 | 36 |
| -035 | Trimellitic Acid Anhydride | 499 | 500 | 12.8 | 53.2 |

*Catalyst is Ni Oxide on Alumina

In TABLE III to follow terephthalic acid process residue (TAR), hereinafter more completely defined, unextracted or water extracted (TARX) is decarboxyl- and decarbonylated in the presence of various catalysts at various temperatures. Again only the total liquid aromatic hydrocarbons and $CO_2$, both in weight percent of sample, are reported. Also a slight flow (about 3 ml/sec) of nitrogen gas is used for the purposes before described.

TABLE III
DECARBOXYLATION AND DECARBONYLATION OF TEREPHTHALIC ACID PROCESS RESIDUES

| | Catalyst | Temperature, °C. Vap. | Temperature, °C. Catalyst | Product, Wt. % Liquid | Product, Wt. % $CO_2$ |
|---|---|---|---|---|---|
| 4789-124 | Copper Wool | 353 | 353 | 0 | 2.29 |
| -125 | $Cu_2O$-wire | 350 | 350 | 0 | 10 |
| -126 | " | 400 | 400 | 0 | 16.6 |
| -134 | Ba Promoted | | | | |

TABLE III-continued
DECARBOXYLATION AND DECARBONYLATION OF TEREPHTHALIC ACID PROCESS RESIDUES

| Catalyst | | Temperature, °C. Vap. | Temperature, °C. Catalyst | Product, Wt. % Liquid | Product, Wt. % $CO_2$ |
|---|---|---|---|---|---|
| | Cu Chromite | 500 | 500 | 0 | 105.6 |
| -132 | Gamma Alumina | 500 | 500 | 0 | 19.8 |
| -128 | Chromia on Gamma Alumina | 400 | 400 | 0 | 14.5 |
| -136 | ZnO-Alumina Co Gel | 500 | 500 | 0 | 3.58 |
| -137 | Chromia Promoted $Fe_2O_3$ | 400 | 400 | 0 | 18.4 |
| -131 | Co-Molybdate on Gamma Alumina | 397 | | 0 | 1.64 |
| -142 | $Co_2O_3$ on Keiselguhr | 398 | 398 | 0 | 30.34 |
| -145 | Ni Oxide on Refractory Support | 399 | 399 | 10.96 | 15.8 |
| -171 | ZnO | 499 | 499 | 28.0 | 23.4 |
| -196 5065-009[1] | ZnO on Alumina | 500 | 500 | 26.0 | 22 |
| -008[1,2] | ZnO on Alumina | 499 | 499 | 26.2 | 30.0 |
| -041[3] | ZnO on Alumina | 502 | 502 | 27.7 | 26.2 |
| -044[4] | ZnO on Alumina | 501 | 501 | 24.0 | 26.7 |
| -026[2] | ZnO on Alumina | 501 | 501 | 28.0 | 31.0 |
| | ZnO on Alumina | 501 | 502 | 30 | 35.8 |
| -027 -034[5] | ZnO on Alumina | 503 | 500 | 26 | 36.4 |
| | ZnO on Alumina | 499 | 504 | 22.9 | 40.4 |

[1]Sample is five grams
[2]Residue from terephthalic acid process after being extracted with water.
[3]Sample is 40.76 grams
[4]Sample is 28.85 grams
[5]Residue from o-phthalic acid process after being extracted with water.

In general, the use of prior suggested decarboxylation catalysts did cause carbon dioxide to be liberated or produced but not all such catalysts caused an attractive co-production of liquid aromatic hydrocarbons. Of those prior suggested decarboxylation catalysts, zinc oxide alone, or zinc oxide in admixture with or supported by chromia or alumina, or a mixture of zinc oxide with either molybdena, or with oxides of cobalt and tungsten supported on molecular sieves in general were found to produce liquid aromatic hydrocarbons in yields upward from about 50 percent of the theoretical yield at temperatures above 450° C. However, the effective life of such better liquid aromatic hydrocarbon producing catalyst was short.

The consistently better prior suggested catalyst was found to be the combination of zinc oxide and alumina. Such catalyst is used at 500° C. with one to two gram samples of terephthalic acid process residues introduced consecutively at about 5-minute intervals into the heated quartz tube containing said catalyst over a five day period. The liquid aromatic hydrocarbon yield decreases from 26.4 weight percent down to 14.6 weight percent of residue fed over the five day period and considerable blackening of the catalyst is observed. Said liquid aromatic hydrocarbon decrease occurs with a residue to catalyst weight ratio of no more than about 2:1. Such results indicate a very short life for the ZnO-alumina catalyst and that frequent regeneration thereof would be necessary for such catalyst to be used commercially.

Such short useful catalyst life made this use thereof for pyrolysis of the aforementioned residues commercially unattractive. However the present inventive non-catalytic pyrolysis of the aromatic acid process residues to useful aromatic hydrocarbons, gaseous hydrocarbons and char is a technically and commercially attractive route for disposal of such residues.

STATEMENT OF THE INVENTION

According to the present invention a mixture of methylol-, aldehydo-, carboxy, keto- and carboxy, and carboxy-methylol-carboxy and aldehydo-substituted benzene and toluene as a solid is introduced in the absence of oxygen into a heating zone wherein the mixture is heated to a temperature of at least 700° C. whereat vapors of said oxygen-containing aromatic compounds are generated and, through pyrolysis alone in the absence of a catalyst, said vapors are converted to normally liquid aromatic hydrocarbons, carbon oxides, hydrogen, at least one of the lower $C_1$ to $C_4$ alkanes and $C_2$ to $C_4$ alkenes, and a solid char. Said heating is accomplished by indirect heat exchange and can be carried out in a stationary tube heated by a furnace. Preferably for batchwise operation, the solids are first heated to 500° C. and the vapors therefore are heated to at least 700° C., e.g., 700° to 900° C. Such can be done by introducing said mixture of oxygen-containing aromatic compounds into the first heating zone, which is at 500° C., either as a small incremental portion as in a ceramic boat or as time spaced sequential batchwise in a sequence of successive small incremental portions as by a piston or ram feeder or bucket, blade or scraper conveyor. For continuous operation, a belt or screw conveyor can be used to transport the solid into and through a heating zone which is at a temperature of from 700° C. up to 900° C. The resulting char is discharged from such heating zone.

Said oxygen-containing solid can be so subjected to continuous pyrolysis at a temperature of at least 700° C. by comminuting such solid into particulates, e.g., particles which will pass through 20 to 30 U.S. Standard Sieves, that is, have a particle size smaller than 0.833 mm diameter but larger than 0.589 mm diameter. Such comminuted solid particles can then be conveyed with an inert carrier gas (e.g., nitrogen) into the bottom of a fluidized bed of inert inorganic particulate solids of similar particle size (e.g., sand, diatomaceous earth or oxides or carbonates of calcium and/or magnesium) heated in one or more zones to at least 700° C. The entire mixture leaving the top of the fluidized bed of inorganic particulates can be separated into a stream of vapors and gases and a heavier stream of inorganic and char particles by centrifugal force, for example, by a cyclone. Also the mixture of comminuted solids and inert particulates can be fed through the hot zone which is at a temperature of from 700° up to 900° C. The separated hot, above 700° C., inorganic and char particulates can be mixed with a source of molecular oxygen; for example, air, oxygen gas or a mixture of oxygen gas and air, to burn the carbonaceous char residue and thereby increase the temperature of the inorganic particles for their return to the fluidized bed of particles. Additional heat for pyrolysis therein may be needed and such additional heat can be supplied in known manner.

It is preferred for batchwise operation that the second heating zone or pyrolysis zone be maintained at a temperature within the range of from 700° C. up to 900° C. and the vapors and gases moved through the heating zones by an inert gas, preferably nitrogen.

Preferred for use in the present invention are the aforementioned residue or water insoluble portion thereof obtained from the manufacture of a benzene di- or tricarboxylic acid through oxidation of a liquid phase of a di- or trialkylbenzene with a source of molecular oxygen (e.g., air and/or oxygen gas) in the presence of a cobalt-containing catalyst.

The mixture of gases and vapors produced by the foregoing pyrolysis can be cooled to a temperature below the boiling temperature of benzene (below 80° C.) to convert to a liquid product the normally liquid hydrocarbons. The remainder of the mixture of gases and vapors, that is, the mixture of carbon oxides, hydrogen and at least one of the $C_1$ to $C_4$ alkanes and $C_2$ to $C_4$ alkenes can be cooled to convert the alkanes and alkenes to a second liquid product or such gas-vapor mixture can be burned to provide a portion of the heat for pyrolysis.

By the present non-catalytic pyrolysis the aforementioned residue is converted into two hydrocarbon-containing products. The first product comprises in addition to carbon oxides and hydrogen and normal gaseous hydrocarbons methane, ethane and ethylene. The second product comprises mainly the normally liquid aromatic hydrocarbons benzene and toluene together with small amounts of biphenyl and lesser amounts of higher molecular weight multi-ring hydrocarbons containing two, three or more aromatic rings as in terphenyl or anthracene.

The resulting mixture of gases and vapors from the present inventive pyrolysis are cooled to about 75° C. or below to condense the aromatic hydrocarbons as a liquid product. The uncondensed mixture comprises mainly oxides of carbon together with some hydrogen, methane, ethylene, ethane and propane.

The present non-catalytic pyrolysis also produces a solid product, char, which contains catalyst metals, bromine if the same is used for catalysis, but is mainly carbon with some hydrogen and oxygen. Unlike an incineration ash, the char can be extracted with acetic acid to remove most of the catalyst metals and, if present, a portion of the bromine. The extracted char together with the uncondensed gases can be burned as fuel to supply the heat for pyrolysis.

Residues from the manufacture of benzene di- and tricarboxylic acids in general contain from zero to five weight percent total of water and acetic acid, from three up to five weight percent total of components of catalyst and associated with the metals (usually in the plus two valence state) from three to ten weight percent acetate radical. Thus, the oxygen-containing aromatic compounds can comprise from 79 to 96 weight percent of the residue.

More specifically, the oxygen-containing aromatic compounds which can be present in the residues subjected to pyrolysis of this invention can be illustrated by the identified compounds present in the residue from the manufacture of terephthalic acid by the air oxidation of p-xylene in acetic acid as reaction solvent and in the presence of cobalt, manganese and bromine as components of the catalyst system. Such identified compounds are now known to be: terephthalic acid and its precursors p-toluic acid, p-formylbenzoic acid, p-tolualdehyde, terephthalaldehyde and p-methylbenzyl alcohol by-products including methylphthalic acids, ortho- and isophthalic acids (from o- and m-xylene impurities in the p-xylene), trimellitic acid, as well as benzaldehyde and benzoic acid (from ethylbenzene impurity in p-xylene); and co-products including 4,4'-bibenzoic acid; 1,2-bis(p-carboxyphenyl)ethane; 2,5,4'-tricarboxybiphenyl; 2,6-dicarboxyfluorenone; and 4,4'-stilbene dicarboxylic acid. On a water and acetic acid free basis one such residue contains the weight percentages of the foregoing compounds and groups of compounds as shown in TABLE IV to follow.

TABLE IV

| COMPONENTS OF RESIDUE FREE OF WATER AND ACETIC ACID | |
|---|---|
| Terephthalic Acid | 26.4% |
| p-Toluic Acids | 20.8% |
| p-Formylbenzoic acid | 9.1% |
| p-Tolualdehyde | 0.51% |
| Terephthalaldehyde | 1.20% |
| p-Methylbenzyl Alcohol | 2.06% |
| Reaction By-Products | 36.9% |
| Co-Products | 4.12% |

Another such residue has the composition including the catalyst components: cobalt, manganese and bromine and metals of corrosion as shown in TABLE V to follow.

TABLE V

| RESIDUE FROM TEREPHTHALIC ACID MANUFACTURE ON ACETIC ACID AND WATER-FREE BASIS | |
|---|---|
| Component | Weight Percent |
| Phthalic Acids | 19.0 |
| Benzoic Acid | 14.8 |
| Toluic Acids | 26.7 |
| Methyl Phthalic Acids | 2.65 |
| Trimellitic and Trimessic Acids | 4.32 |
| 4-Carboxybenzaldehyde | 9.09 |
| Tolualdehydes | 0.40 |
| Benzaldehyde | 0.004 |
| Terephthalaldehyde | 0.27 |
| Methylbenzyl Acetate | 0.02 |
| Formyl Acetate | 0.15 |
| Benzylbenzoate | 0.07 |
| Phthalide | 2.04 |
| Co-Products | 4.24 |
| Cobalt | 1.51 |
| Manganese | 2.53 |
| Bromine | 2.20 |
| Iron | 0.09 |
| Aluminum | 0.00022 |
| Calcium | 0.02 |
| Chromium | 0.007 |
| Copper | 0.0001 |
| Magnesium | 0.0028 |
| Molybdenum | 0.0035 |
| Sodium | 0.30 |
| Nickel | 0.0052 |
| Silica | 0.0025 |
| Anion of Metals | 9.04 |

The first four elements are determined by X-ray fluorescence and the remaining elements are determined by emission spectroscopy. The foregoing more detailed identification of organic components and metals is not one usually made by terephthalic acid manufacturing facilities but is made for research purposes as a starting point, for example, to identify extractable components, or to evaluate the completeness of commercial oxidation of the xylene feed, or to evaluate potential increase of phthalic acids production by some additional oxidation of the phthalic acid precursors present in such residue.

However, the terephthalic acid manufacturing facilities will obtain a partial analysis of the residue to include at least the phthalic acids, toluic acids, benzoic acid and catalyst components to determine on a day-to-day basis the approximate oxidation efficiency, and catalyst metal and solvent discard. Such partial analytical inspections of the residue are as shown in TABLE VI to follow.

TABLE VI

PARTIAL ANALYTICAL RESULTS OF RESIDUE FROM TEREPHTHALIC ACID MANUFACTURE

| Components | Sample Number | | | |
|---|---|---|---|---|
| In Weight % | 1 | 2 | 3 | 4 |
| Acetic Acid | 0.22 | 3.23 | 3.74 | 3.24 |
| Phthalic Acids | 45.8 | 31.4 | 33.4 | 26.0 |
| Toluic Acids | 5.2 | 12.3 | 12.9 | 22.6 |
| 4-CBA[1] | 1.05 | 4.56 | 4.82 | 9.1 |
| Benzoic Acid | 20.2 | 27.6 | 26.0 | 19.8 |
| Trimellitic Acid | 5.4 | 4.0 | 4.3 | 3.8 |
| OLB Compounds[2] | 0.2 | 4.1 | 4.4 | 0.9 |
| HB Compounds[3] | — | 7.5 | 5.8 | 0.4 |
| Cobalt | 0.69 | 0.49 | 0.5 | 1.35 |
| Manganese | 1.79 | 1.22 | 1.3 | 2.48 |
| Bromine | 2.59 | 1.49 | 1.5 | 2.5 |

[1] "4-CBA" is 4-carboxybenzaldehyde (p-formylbenzoic acid).
[2] "OLB Compounds" are other lower boiling compounds.
[3] "HB Compounds" are higher boiling (higher than trimellitic acid) compounds.

The residue from manufacture of isophthalic acid by air oxidation of m-xylene in an acetic acid reaction medium and in the presence of catalysis provided by cobalt, manganese and bromine is quite similar to the residue from the manufacture of terephthalic acid by the same oxidation of p-xylene. The manufacture of the anhydride (intramolecular) of trimellitic acid (TMA) can produce two residues. One residue is obtained after precipitating and separating impure trimellitic acid from the acetic acid solution of the catalyst (Co-Mn-Br) system and then evaporating the acetic acid. The second residue is obtained after dehydration of impure trimellitic acid (TMLA) to its impure anhydride and evaporating a partially purified anhydride. The compositions of such TMLA and TMA residues and the residue from isophthalic acid (IA) manufacture are characterized in TABLE VII to follow.

TABLE VII

CHARACTERIZATION OF RESIDUES FROM THE MANUFACTURE OF ISO-PHTHALIC ACID AND TRIMELLITIC ANHYDRIDE

| Component, | RESIDUE | | |
|---|---|---|---|
| In Weight % | IA | TMLA | TMA |
| Acetic Acids | 0.11 | 1.58 | 0 |
| Phthalic Acids | 39.8 | 12.3 | 1.0 |
| Toluic Acids | 1.8 | 0 | 0 |
| Aldehydes | 0.09 | 0.53 | 1.4 |
| Benzoic Acid | 24.1 | 0.5 | 0 |
| Trimellitic Acid | 2.5 | 38.6 | 65.2[1] |
| OLB Compounds[2] | 1.7 | 4.7 | 1.9 |
| HB Compounds[2] | 5.3 | 0.94 | 0.4 |
| Cobalt | 0.48 | 1.17 | 2.51 |
| Manganese | 1.27 | 0.28 | 0.87 |
| Bromine | 2.6 | 0.94 | 0.15 |

[1] Trimellitic acid anhydride
[2] See TABLE VI

The residues from the manufacture of phthalic anhydride of interest for use in the practice of the present invention are obtained from two different oxidation processes. The residue from the first of such processes is obtained after evaporation of acetic acid and water from the liquid portion of the oxidation effluent from the air oxidation of o-xylene in an acetic acid solution of the Co-Mn-Br catalyst system after precipitating and recovering o-phthalic acid or its anhydride from the oxidation effluent. Such residue contains the components and their concentrations substantially the same as in the residues characterized by TABLES IV through VII. The residue from the second type of oxidation process is obtained by heating the oxidation effluent to convert o-phthalic acid to its anhydride and evaporate the anhydride and water when such effluent is produced by the air oxidation of liquid o-xylene in liquid o-phthalic acid containing the Co-Mn-Br system of catalysis. Since such oxidation does not use an extraneous solvent, it is hereafter sometimes referred to as the "neat oxidation" process. Such residue from the second type of oxidation process comprises 50 to 85 weight percent phthalic anhydride as a flux for higher boiling materials; e.g., iso- and terephthalic acid, trimellitic acid, metal (Co and Mn) phthalates or acetates, and oxygen-containing both coupled and fused ring compounds: di-, tri- and tetracarboxy-substituted biphenyl and benzophenone and dicarboxyfluorenone. In TABLE VIII to follow there are given the components and their concentrations in weight percent of such residues from said second type of o-xylene oxidation process.

In TABLE VIII "PAN" is used to designate phthalic anhydride and "2-CBA" is used to designate 2-carboxybenzaldehyde.

TABLE VIII

NEAT OXIDATION RESIDUES

| Component | Residue Number | | | | |
|---|---|---|---|---|---|
| Weight % | 1 | 2 | 3 | 4 | 5 |
| PAN | 72.2 | 77.4 | 65.7 | 84.5 | 57.3 |
| o-Toluic Acid | 0.03 | 0.23 | 0.15 | 0.04 | 0.1 |
| Phthalide | 0.01 | 0.2 | 0.18 | 0.001 | 0.3 |
| 2-CBA | 0.77 | 1.0 | 1.03 | 0.41 | 1.65 |
| Benzoic Acid | 0.56 | 1.03 | 0.69 | 0.60 | 1.8 |
| Other Aromatics | 20.7 | 16.0 | 26.8 | 11.5 | 22.7 |
| Cobalt | 1.14 | 1.08 | 1.36 | 0.62 | 0.58 |
| Manganese | 3.38 | 2.29 | 3.34 | 1.85 | 1.13 |
| Bromine | 1.32 | 0.90 | 0.78 | 0.87 | 1.01 |

Also useful in the practice of the present inventive pyrolysis are the undissolved solids portion of the residues after the extraction of the residues with water to remove catalyst metals for reuse in the oxidation from which the metal-containing residue originated. Such undissolved solids portion is hereafter referred to as "extracted residue". In TABLE IX to follow characteristics of such extracted residues are given.

TABLE IX

EXTRACTED RESIDUES

| Components | Of Sample 1 | Of Sample 3 | of Neat Oxidn. |
|---|---|---|---|
| Weight % | TABLE VI | TABLE VI | Residue |
| Aldehydes | 1.57 | 5.84 | 1.03 |
| Benzoic Acid | 18.1 | 31.4 | 1.7 |
| Toluic Acids | 1.61 | 16.0 | 0 |
| Phthalic Acids | 56.4 | 37.6 | 5.6 |
| OLB Compounds | 0.4 | 0.78 | 41.0 |
| HB Compounds | 8.0 | 3.6 | 0.2 |
| Cobalt | 0.18 | 0.03 | 0.16 |
| Manganese | 0.49 | 0.10 | 0.28 |
| Bromine | 0.51 | 0.09 | 0.35 |

Non-catalytic pyrolysis of the before described residues from benzene di- and tricarboxylic acid manufacture would be more attractive commercially, provided the yield of liquid aromatic hydrocarbons would be equal to or better than the liquid aromatic hydrocarbon yield from the before described five day test of the ZnO on alumina catalyst.

ILLUSTRATION OF THE INVENTION

The following examples are presented to illustrate the practice of the present invention non-catalytic pyrolysis conducted on a batchwise basis.

In the examples to follow the pyrolysis was conducted in a quartz tube having a 21 mm internal diameter, a 2 mm wall thickness and a 96.5 cm length fitted with internal thermocouple wells to provide accurate measurement of vaporization (first heating zone) and pyrolysis (second heating zone) temperatures. A clean quartz tube is used for each example. The pyrolysis quartz tube is heated in two equal (30.5 cm) portions of its length by two electric furnaces. Introduction of the comminuted residue solids into the pyrolysis tube is accomplished as described in connection with and prior to the experiments reported in TABLES I and II. A nitrogen gas flow of 1 to 10 ml/sec. through the tube is maintained to sweep vapors and gases through the two heating zones, the two traps cooled with a slurry of solid $CO_2$ in isopropanol, and a drier to remove any water vapor uncondensed to a gas collector. Measured samples of the collected gas are analyzed by mass spectrometry. The amount of $CO_2$ generated was determined gravimetrically by adsorption of $CO_2$ by 20-30 mesh sodium hydroxide asbestos absorbent. The aromatic liquids collected in the $CO_2$-isopropanol cooled traps are analyzed by gas chromatography using the simulated distillation method of ASTM Method D-2887-73. The pyrolysis tube was over the second heating zone packed with quartz chips instead of quartz wool.

The results are shown in TABLES X–XIII of the non-catalytic batchwise decarboxylation-decarbonylation processes using a residue from the manufacture of terephthalic acid (TAR) having the components of Sample No. 3 of TABLE VI. Both of said types of solid residues were comminuted to pass through a screen having 0.833 mm openings.

TABLE X

NON-CATALYTIC DECARBOXYLATION-DECARBONYLATION OF SAMPLE NO. 3 - TABLE IX COMMINUTED TO LESS THAN 0.83 mm

| Example No. | 1 | 2 | 3 | 4 | 5 | 6 | 7 |
|---|---|---|---|---|---|---|---|
| Temperature: | | | | | | | |
| First Zone, °C. | 500 | 500 | 500 | 500 | 500 | 500 | 500 |
| Second Zone, °C. | 751 | 748 | 794 | 796 | 751 | 797 | 798 |
| Residue Charge, gm | 28.7 | 35.9 | 31.0 | 34.4 | 21.8 | 33.3 | 33.7 |
| $N_2$ Flow, ml/sec. | 2.9 | 2.9 | 2.9 | 2.9 | 1.0 | 10.0 | 10.0 |
| Char, gm | 4.0 | 8.0 | 4.6 | 6.6 | 4.2 | 5.9 | 5.8 |
| Wt. % Residue | 13.9 | 22.3 | 14.8 | 19.2 | 19.3 | 17.7 | 17.2 |
| $CO_2$, gm | 8.5 | (1) | 8.8 | (1) | (1) | 10 | (1) |
| Trapped Liquids, gm: | 11.8 | 13.9 | 10.4 | 12.5 | 7.3 | 10.4 | 10.4 |
| Benzene, wt. % | 66 | 69 | 73 | 71 | 70 | 76 | 78 |
| Toluene, wt. % | 15 | 17 | 16 | 15 | 18 | 13 | 14 |
| H.B. (2), wt. % | 19 | 14 | 11 | 14 | 12 | 11 | 8 |
| Wt. % of Residue | 41.1 | 38.7 | 33.5 | 36.3 | 35.7 | 31.2 | 30.9 |
| Gases, wt. % | | (1) | | (1) | (1) | | (1) |
| $H_2$ | 0.1 | | 0.1 | | | 0.1 | |
| CO | 3.0 | | 3.2 | | | 2.7 | |
| $CH_4$ | 0.6 | | 0.7 | | | 0 | |
| $C_2H_4$ | 0.2 | | 0.3 | | | 0.3 | |
| $C_2H_6$ | 0.1 | | 0.1 | | | 0 | |

(1) Not Measured
(2) "H.B." are higher boiling aromatics, i.e. boil above toluene.

In TABLE XI to follow, Example 8 is from the non-catalytic pyrolysis of TAR. Sample No. 3 of TABLE VI and Example 9 is from the non-catalytic pyrolysis of Extracted TAR similar to Sample No. 3 of TABLE IX.

TABLE XI

| Example No. | 8 | 9 |
|---|---|---|
| Temperature: | | |
| First Zone, °C. | 500 | 500 |
| Second Zone, °C. | 749 | 750 |
| Material Charge, gm | 38.8 | 40.0 |
| $N_2$ Flow, ml/sec. | 2.9 | 1.0 |
| Char, gm | 6.1 | 10.4 |
| Wt. % Residue | 15.5 | 26.1 |
| $CO_2$, gm | 13.6 | 8.8 |
| Trapped Liquid, gm | 14.3 | 15.6 |
| Benzene, wt. % | 58.8 | 55.5 |
| Toluene, wt. % | 14.1 | 6.7 |
| H.B.(2), wt. % | 27.1 | 37.8 |
| Wt. % of Residue | 37.1 | 39.1 |
| Gases, wt. % | | |
| $H_2$ | 0.1 | 0.1 |
| CO | 3.4 | 3.7 |
| $CH_4$ | (1) | (1) |
| $C_2H_4$ | (1) | (1) |
| $C_2H_6$ | (1) | (1) |

(1) Not Measured.
(2) It is noted that of the trapped liquids in Examples 8 and 9 those obtained from the residue (Example 8) are substantially higher in toluene and lower in higher boiling aromatics content.

The process of this invention, as previously stated, can readily be conducted on a continuous basis. Such continuous operation is illustrated by Example 9 (TABLE XII) together with comparative Examples I to III which establish the criticality of the lower (at least 700° C.) temperature limit for the non-catalytic pyrolysis. In these (Comparative and Illustrative) examples, the material charged to pyrolysis is the residue (Sample 3, TABLE VI) from terephthalic acid manufacture.

The continuous non-catalytic pyrolysis is conducted in a 16 mm internal diameter stainless steel tube having a wall thickness of 3 mm, a length of 900 mm of which 380 mm is heated in an electric furnace, a conical feed hopper in flow communication with the inlet at one end of the tube, an outlet at the other end of the tube for discharge of char and an internal 12.7 mm diameter stainless steel helical screw driven by a variable speed chain drive. The screw transports the residue from the bottom of the feed hopper through the tube and, as decarboxylation and decarbonylation progress during the non-catalytic pyrolysis, transports the resulting char and any carrier particulates out of the tube to the discharge outlet. Nitrogen gas flow at a rate of 2.9 ml/sec. is provided for flow through the feed hopper and pyrolysis tube. Provisions are made to collect the char, the liquid aromatic hydrocarbon trapped by cooling with a slurry of solid carbon dioxide in isopropanol.

The screw drive is adjusted for a 10–15 minute flow of residue through the tube which provides a residence time in the hottest portion of the tube of about 5 minutes. Carbon dioxide is trapped by asbestos-sodium hydroxide absorbent which is assayed gravimetrically. The liquids collected by the $CO_2$-isopropanol traps and the gas passing through the system are analyzed as before described.

During decarboxylation and decarbonylation the residue melts and while such thermal decomposition is occurring a porous char forms which tends to stick to the walls of the tube and the hot surfaces of the screw conveyor. To prevent plugging of the tube a particulate, inert, and thermally stable solid is used as a carrier. In these continuous operations, diatomaceous earth and silica sand are used as solid carriers for the porous char. The amount of char formed can then be determined gravimetrically from the before and after use weights of the carrier. Two carriers are used; a diatomaceous earth (A) and a silica sand (B), each of from 0.589 to 0.833 mm diameter. The residue from terephthalic acid manufacture is comminuted to smaller than 0.833 mm diameter but larger than 0.701 mm diameter (i.e., to pass through U.S. Sieve of 20 mesh but collect on U.S. Sieve of 25 mesh), mixed with the carrier in the weight ratio of A to residue of 3:1 and B (sand) to residue to 6:1.

TABLE XII

| | CONTINUOUS PYROLYSIS | | | |
| | Comparative | | | Illustrative |
| Example | I | II | III | 10 |
|---|---|---|---|---|
| Carrier | A | A | A | B |
| Ratio to Residue | 3:1 | 3:1 | 3:1 | 6:1 |
| Pyrolysis, °C. | 501 | 553 | 600 | 750 |
| Residue Charge, gm | 50 | 50 | 50 | 100 |
| $N_2$ Flow, ml/sec. | 2.9 | 2.9 | 2.9 | 2.9 |
| Char, gm | 18.4 | 22.3 | 14.6 | 7.7 |
| Wt. % Residue | 36.8 | 44.6 | 29.2 | 7.7 |
| $CO_2$, gm | 11.9 | 18.5 | 16.1 | 34.2 |
| $CO_2$ wt. % Residue | 23.8 | 37.0 | 32.3 | 34.2 |
| Trapped Liquid, gm | 3.6 | 5.3 | 10.8 | 25.5 |
| Benzene, wt. % | ND | 87 | 40 | 72 |
| Toluene, wt. % | ND | 8 | 18 | 14 |
| H.B. Aromatics, wt. % | ND | 5 | 42 | 14 |
| Wt. % of Residue | 7.2 | 10.6 | 21.6 | 25.5 |

"N.D." is not determined because of low yield.

The catalyst metals cobalt and manganese together with contaminant metals iron, nickel and chromium can usually be extracted with water from the residue from benzene di- and tricarboxylic acid manufacture. But, water is not an efficient extracting solvent to remove catalyst metals from the char products of the present inventive non-catalytic pyrolysis. However we have discovered that acetic acid is efficient for extracting catalyst metals from the char product of the present inventive process. The differences in efficiency for extracting catalyst metals from the char is illustrated by data presented in TABLE XIII to follow. The char is extracted with water at 98° C. using a weight ratio of water to char of 20.0:1.0 or with acetic acid at 103° C. using a weight ratio of acetic acid to char of 21.6:1.0.

TABLE XIII

| EXTRACTION OF CHAR WITH WATER OR ACETIC ACID | | | | |
|---|---|---|---|---|
| Extract | Element Extracted, wt. % | | | |
| Solvent | Br | Co | Mn | Fe |
| Water | 90 | 4 | 13 | 4.1 |
| Acetic Acid | 68.7 | 66.5 | 76.2 | 60.1 |

The invention claimed is:

1. A method of decarbonylating and/or decarboxylating a mixture containing aldehydo-, carboxy-, methylol-, keto- and carboxy-, methylol-carboxy-, and carboxy- and aldehydo-substituted benzene and toluene which comprises heating such mixture in the absence of an externally added catalyst to a temperature of at least 700° C. whereat there is formed a solid carbonaceous product and a hydrocarbon product including vapors of benzene and toluene together with lower alkanes and alkenes, hydrogen and oxides of carbon; and collecting at least vapors of benzene and toluene.

2. The method of claim 1 wherein the solid carbonaceous product and the hydrocarbon product, after collecting benzene and toluene and removing carbon dioxide, are burned to provide heat for the decarbonylation and decarboxylation.

3. The method of claim 1 wherein such mixture also contains acid salts of cobalt and manganese and organic and inorganic bromides, the solid carbonaceous product is extracted with acetic acid and then burned to provide heat for the decarbonylation and decarboxylation.

4. The method of claim 3 wherein such mixture is first heated to a temperature of 500° C. and the vapors and gases therefrom are heated to a temperature of from 700° C. up to 900° C.

5. The method of claim 2 wherein such mixture is obtained from the manufacture of terephthalic acid and also contains acid salts of cobalt and manganese and organic and inorganic bromides.

6. The method of claim 1 wherein such mixture is obtained from the manufacture of terephthalic acid and also contains acid salts of cobalt and manganese and inorganic and organic bromides, is comminuted and diluted with an inert particulate solid, and the diluted mixture is continuously fed through a zone heated to a temperature of from 700° C. up to 900° C.

* * * * *

UNITED STATES PATENT OFFICE
CERTIFICATE OF CORRECTION

Patent No. 4,266,084  Dated May 5, 1981

Inventor(s) John K. Allen

It is certified that error appears in the above-identified patent and that said Letters Patent are hereby corrected as shown below:

Patent Reads:

| Col. | Line | | |
|---|---|---|---|
| 2 | 19 | "next oxidation" should be | -- neat oxidation -- |
| 2 | 28 | "substantially" should be | -- substantial -- |
| 2 | 52-53 | "and-/or" should be | -- and/or -- |
| 3 | 59 (Table) | "3.8" should be | -- 35.8 -- |
| 11 | 4 | "invention" should be | -- inventive -- |
| 13 | 12 | "to 6:1" should be | -- of 6:1 -- |
| 6 | 9 | "carboxy" (1st. occurrence) should be | -- carboxy- -- |

Signed and Sealed this

Nineteenth Day of October 1982

[SEAL]

Attest:

Attesting Officer

GERALD J. MOSSINGHOFF

Commissioner of Patents and Trademarks